United States Patent [19]
Robinson et al.

[11] Patent Number: 6,017,521
[45] Date of Patent: Jan. 25, 2000

[54] USE OF POLYCARBOXYLIC ACID POLYMERS TO TREAT VAGINAL INFECTIONS

[75] Inventors: Joseph R. Robinson, Madison, Wis.; William J. Bologna, NY, N.Y.

[73] Assignee: Columbia Laboratories, Inc., Aventura, Fla.

[21] Appl. No.: 08/951,419

[22] Filed: Oct. 16, 1997

Related U.S. Application Data

[63] Continuation of application No. 07/939,454, Sep. 2, 1992, abandoned, which is a continuation-in-part of application No. 07/732,738, Jul. 18, 1991, abandoned, which is a continuation of application No. 07/429,755, Oct. 31, 1989, abandoned, and a continuation-in-part of application No. 07/732,739, Jul. 18, 1991, abandoned, which is a continuation of application No. 07/429,770, Oct. 31, 1989, abandoned.

[51] Int. Cl.[7] .................................................. A61K 31/78
[52] U.S. Cl. ..................................... 424/78.02; 424/78.07; 424/430; 514/967
[58] Field of Search ............................. 424/78.02, 78.07, 424/430

[56] References Cited

U.S. PATENT DOCUMENTS

| | | | |
|---|---|---|---|
| 2,923,692 | 2/1960 | Ackerman et al. | 524/548 |
| 4,032,269 | 6/1977 | Osberghaus . | |
| 4,296,096 | 10/1981 | Pierce . | |
| 4,548,990 | 10/1985 | Mueller . | |
| 4,552,755 | 11/1985 | Randen | 514/195.1 |
| 4,597,965 | 7/1986 | Holly . | |
| 4,615,697 | 10/1986 | Robinson | 604/890 |
| 4,698,359 | 10/1987 | Niederer et al. . | |
| 4,863,725 | 9/1989 | Deckner et al. . | |
| 4,900,554 | 2/1990 | Yanagabashi . | |
| 4,933,182 | 6/1990 | Higashi et al. | 424/435 |
| 5,143,731 | 9/1992 | Viegas et al. | 514/967 |

FOREIGN PATENT DOCUMENTS

| | | |
|---|---|---|
| 6172706 | 4/1986 | Japan . |
| 8906964 | 8/1989 | WIPO . |
| 8906964 | 10/1989 | WIPO . |

OTHER PUBLICATIONS

6001 Chemical Abstracts 99 (1983) Oct. No. 14, Columbus, Ohio, USA.

Breen, J., ed. *The Gynecologist and the Older Patient*, pp. 304–305 (1988).

Kaufman et al., *Benign Diseases of the Vulva and the Vagina*, 3rd ed., pp. 401–418 (1989).

Barbone et al.,"A Follow–up Study of Methods of Contraception, Sexual Activity and Rates of Trichomoniasis, Candidiasis and Bacterial Vaginosis," *Am. J. Obstet. Gynecol.*, vol. 163, No. 2, p. 515 (Aug. 1990).

Andersen et al., "Treatment of Bacterial Vaginosis with an Acid Cream: A Comparison between the Effect of Lactate Gel and Metronidazole", *Gynecol. Obstet. Invest.*, 21:19–25 (1986).

Zinny, M. and Lee, S., "Double–Blind Study of the Comparative Effects of Two Gels on Vaginal pH in Postmenopausal Women", *Today's Therapeutic Trends*, 8(4):65–72 (1992).

Bachmann et al., "Vaginal Dryness in Menopausal Wioemn: Clinical Characteristiccs and Nonhormonal Treatment", *Clinical Practice in Sexuality*, vol. 7, No. 9, 1–8 (1991).

*Primary Examiner*—Peter F. Kulkosky
*Attorney, Agent, or Firm*—Fulbright & Jaworski L.L.P.

[57] ABSTRACT

The present invention relates to the use of a bioadhesive aqueous composition to control the pH of the vagina to alleviate microorganism growth and feminine odor such as presented by bacterial vaginosis. The composition contemplated herein comprises water and an acidic polymer, specifically one wherein 80% of the monomers contain at least one carboxyl group [—COOH] and wherein the polymer is cross-linked so as to be water-swellable, but water-insoluble. The composition of the present invention is additionally a bioadhesive providing for a long-lasting benefit and control of vaginal pH.

13 Claims, 9 Drawing Sheets

USE OF POLYCARBOXYLIC ACID POLYMERS TO TREAT VAGINAL INFECTIONS

This application is a continuation, of appliction Ser. No. 07/939,454, filed Sep. 2, 1992, now abandoned, which is a continuation-in-part of appliction Ser. No. 07/732,738, filed Jul. 18, 1991, now abandoned, which is a continuation of application Ser. No. 07/429,755, filed Oct. 31, 1989, now abandoned, and a continuation-in-part of application Ser. No. 07/732,739, filed Jul. 18, 1991, now abandoned, which is a continuation of application Ser. No. 07/429,770, filed Oct. 31, 1989, now abandoned.

BACKGROUND OF THE INVENTION

Bacterial vaginosis is the most common form of infectious vaginitis, accounting for 45% of symptomatic cases and estimated to be present in 15% of asymptomatic sexually active women. See Breen, J., ed., *The Gynecologist and the Older Patient*, pp. 304–305 (1988). Bacterial vaginosis (also called nonspecific vaginitis) is a polymicrobial vaginal infection believed to be caused by an increase in the number of anaerobic organisms with a concomitant decrease in lactobacilli in the vagina. The decrease in the number of lactobacilli in the vagina has a dual effect, i.e., (i) a decreased competition for nutrients and (ii) a decrease in the amount of lactic acid present, thus allowing for the multiplication of opportunistic pathogens in the vagina, whose growth is normally suppressed by the lactobacilli. The principal pathogens associated with bacterial vaginosis are believed to be *Gardnerella vaginalis* and anaerobes of the Mobiluncus species. However, numerous other pathogenic anaerobes are also believed to be involved in the etiology of vaginosis. See Kaufman et al., *Benign Diseases of the Vulva and Vagina*, 3rd ed., pp. 401–418 (1989). Thus, bacterial vaginosis is considered a broad spectrum infection requiring a broad spectrum treatment.

Clinically, bacterial vaginosis presents itself as a superficial vaginal infection with few irrative symptoms and no inflammatory response. Some noticeable symptoms include an unpleasant smell, an elevated vaginal pH greater than about 5.0, a thin homogeneous discharge, the presence of Gardnerella clue cells and a high succinate/lactate ratio ($\geq 0.4$). See, e.g., Livengood et al., "Bacterial Vaginosis: Diagnostic and Pathogenic findings during Topical Clindamycin Therapy," *Am. J. Obstet. Gynecol.*, vol. 163, No. 2, p. 515 (August 1990).

It is believed that the composition of organic acids in the vagina shifts from primarily lactic acid ($pK_a=3.86$) to succinic acid ($pK_{a1}=4.21$, $pK_{a2}=5.64$) as a result of the decrease in the lactobacilli, which produce lactic acid, and a rise in Mobiluncus, which produce succinic acid. This shift in acid composition tends to raise the pH of the vagina. It is unclear whether the change in acidity is a cause or effect of the infection. However, it is known that certain anaerobes will grow better at a higher pH than is normally present in the vagina. It is thus believed that lowering the vaginal pH is an effective measure against the infection.

Moreover, the odor of the amines which are produced in the vagina is known to increase at higher pH's because unprotonated, volatile, amines are present in basic conditions. Additionally, the high pH level is thought to allow the anaerobes to grow and produce the amines that are present in a bacterial vaginosis infection.

Generally, current treatment regimens for bacterial infection of the vagina, including vaginosis, involve the use of various broad spectrum antibiotics, most particularly metronidazole, administered either topically or orally. Antibiotics are undesirable, however, because they may kill a broad range of the normal bacterial flora in the vagina, including the beneficial lactobacilli. This may cause secondary complications, since the lactobacilli keep various opportunistic pathogens in the vagina, such as the yeasts *Candida albicans* and *Torulopsis glabrata* and some anaerobes, including, perhaps, the Mobiluncus in check.

The treatment might then necessitate a further treatment regimen, such as the ingestion of cultured dairy products to replace the lactobacilli in the body, as well as treatment by antifungal agents. Moreover, a rise in the level of anaerobes due to a lack of lactobacilli could further complicate the current infection.

Additionally, if antibiotics are taken orally, other beneficial bacteria in the body, e.g., the *E. coli* in the gastrointestinal tract, may be killed. This can result in gastrointestinal upset (e.g., diahorrea), a common side effect of metronidazole, and further discomforts, if not worse.

Moreover, the use of antibiotics to treat relatively benign infections, such as vaginosis, particularly when systemically administered, is disfavored since such treatment can cause other, more pathogenic bacteria to develop resistance to the antibiotic, which would then not be effective when an antibiotic is really needed to treat a serious bacterial infection in a patient.

Douches comprising hydrogen peroxide have shown some effectiveness as treatments against bacterial vaginosis. See, Kaufman, at 415. However, vinegar douches have been used without much success.

Topically administered creams comprising sulfa drugs also have been used as a means of treating bacterial vaginosis. The acidity of the drugs is thought to provide their limited effectiveness in treating vaginosis. See, e.g., *Older Patient* at 305. Moreover, the relative toxicity of sulfa drugs render them undesirable for treatment of such non-life threatening, although unpleasant, bacterial diseases. Topically administered nonoxynol-9, a spermicide, has also shown limited efficacy in preventing the transmission of bacterial vaginosis. See Barbone et al., "A Follow-up Study of Methods of Contraception, Sexual Activity and Rates of Trichomoniasis, Candidiasis and Bacterial Vaginosis," *Am. J. Obstet. Gynecol.*, Vol. 163, No. 2, p. 510 (August 1990).

In one study, women with bacterial vaginosis were treated topically with an acidic gel. Andersch et al. "Treatment of Bacterial Vaginosis with an Acid Cream: A Comparison between the Effect of Lactate-Gel and Metronidazole", *Gynecol Obstet Invest* 21:19–25 (1986). Following a diagnosis of bacterial vaginosis, as determined by odor, pH and cell cultures, women in the study were treated with either a daily topical treatment of a lactate-gel, buffered to a pH of 3.5, or with 500 mg metronidazole, given orally twice a day (500×2).

The efficacy against bacterial vaginosis of both treatment regimens were compared and found to be similar. However, it was found that the gel had an effect only on the number of anaerobes and not the Gardneralla nor the helpful lactobacilli. Moreover, none of the side effects, such as the nausea reported in 30% of those women taking metronidazole, occurred in women using the gel.

While the above described study indicates that agents that cause a reduction in vaginal pH can be beneficial in the treatment of vaginosis, the problem with such aforementioned topical applications and douches is that the vagina has a clearance time of 30–90 minutes, so that all the contents of the vagina will be expelled therefrom within that time period. Thus, topical treatments and douche ingredients will be expelled from the vagina quickly, leaving the vagina vulnerable to a resurgence of infectious growth. A topical application that would remain in place for greater than 90 minutes would be of great benefit.

In addition, the assignees of the present invention commissioned a study wherein the vaginal pH of postmenopausal women was lowered over an extended period of time by application of REPLENS®, a product made and used according to a parent application of the present application, U.S. application Ser. No. 07/732,738, which contains a cross-linked polycarboxylic acid, polycarbophil, as compared to the application of KY JELLY®. See Zinny, M. and Lee, S., "Double-Blind Study of the Comparative Effects of Two Gels on Vaginal pH in Postmenopausal Women", Today's Therapeutic Trends 8(4): 65–72, 1991. However, this study dealt with postmenopausal women, in whom, due to estrogren deficiency, there is a low level of glycogen, and thereby a low level of lactobacilli and a relatively high vaginal pH. (See Kaufman, p. 420). The different vaginal flora present in postmenopausal women often presents different difficulties in treating vaginal conditions in post-menopausal women than in pre-menopausal women.

Agents that would remain in the vagina for more than 90 minutes include bioadhesives, e.g., such as those cross-linked polycarboxylic acid polymers disclosed as carriers for treating agents in U.S. Pat. No. 4,615,697. While the use of such bioadhesives is known in the art to deliver drugs, they were not known as pH buffers. The bioadhesive effect of the polymers is useful in the present application of these polymers to keep the polymers in place on the vaginal lining. This results in an extended maintenance of an acidic pH in the vagina which ultimately can result in a reduction in the numbers of the microbes involved in the causation of vaginosis. The bioadhesive properties of the polymer prevent it from being rapidly cleared from the vagina as occurs with other topically applied agents. Thus, the present invention provides a novel use of these bioadhesive polymers to maintain the pH of the vagina for long periods of time which reduces the numbers of harmful microorganisms that cause vaginosis and prevents the unpleasant odor attendant to vaginosis without resorting to antibiotics.

SUMMARY OF THE INVENTION

The present invention provides a composition and method for inducing and maintaining an acidic pH in the vagina in order to control the growth of microorganisms that cause vaginosis and vaginal odor. In accordance with the method, the cells lining the vagina are contacted with an aqueous buffering composition that comprises water, an effective pH buffering amount of a water-swellable but water-insoluble cross-linked bioadhesive polycarboxylic acid polymer and, preferably, a thickening/smoothening amount of a consistency-enhancing agent. The pH buffering polymer is a water-swellable, but water-insoluble, cross-linked carboxy-functional polymer. The polymer is used to contact the cells lining the vagina of a mammal, preferably a human.

The pH buffering polymer preferably contains a plurality of monomers of which at least about 80 percent, and preferably at least about 90 percent, contain at least one carboxyl functionality [—COOH], and a cross-linking agent, present in an amount so as to make the polymer water-swellable but water-insoluble. The consistency-enhancing agent is a water-dispersible, and preferably, a water-soluble, non-ionic or anionic polymer.

As noted above, the pH buffering polymer is water-insoluble, which means that less than 1 percent of it dissolves in water, and water-swellable, which means that it generally can absorb about 40 to about 100 times its weight in water. The polymer of the present invention may be contrasted with the water-swellable polymers, that can absorb considerably in excess of 100 times their weight in water, which are not contemplated by the present invention.

In practice, it is preferred that the dry pH buffering polymer is sized to pass through a No. 400 sieve screen (U.S. Standard Sieve Series). It is also preferred that, when in use, the buffering particles be dispersed in a physiologically tolerable diluent, and particularly, an aqueous diluent. The diluent solution may also contain other ingredients useful for application to the vaginal lining.

One advantage of the present invention is that the active pH buffering component of the composition is a bioadhesive, such that, when applied topically to the cells lining the vagina, the composition will remain in place for up to about 2–3 days, providing for long-lasting treatment. Thus, fewer applications of the pH buffering bioadhesive polymer are required for full efficacy than with previously known topically applied compositions to obtain a satisfactory result.

Another advantage of the present invention is that, even though the compositions are acidic in nature, they are not noticeably irritating to the vaginal mucosa with which they are in contact.

A further advantage is that the need for antibiotics to treat vaginosis is reduced, since the acidic environment established in the vagina by the bioadhesive polymer controls growth of the microorganisms causing vaginosis. Moreover, the acidic environment also produce protonation of the odoriferous amines resulting in the production of non-volatile and non-odoriferous salts of the odor-producing amines in the vagina, thereby decreasing the offensive odor resulting from vaginosis.

A still further advantage is that the polymer of the present invention provides moisturization to the vagina.

Still further advantages of the present invention will be apparent to those skilled in the art from the Detailed Description, Examples and Claims that follow.

BRIEF DESCRIPTION OF THE DRAWINGS

In the figures forming a part of this disclosure.

DETAILED DESCRIPTION OF THE INVENTION

Figure 1:
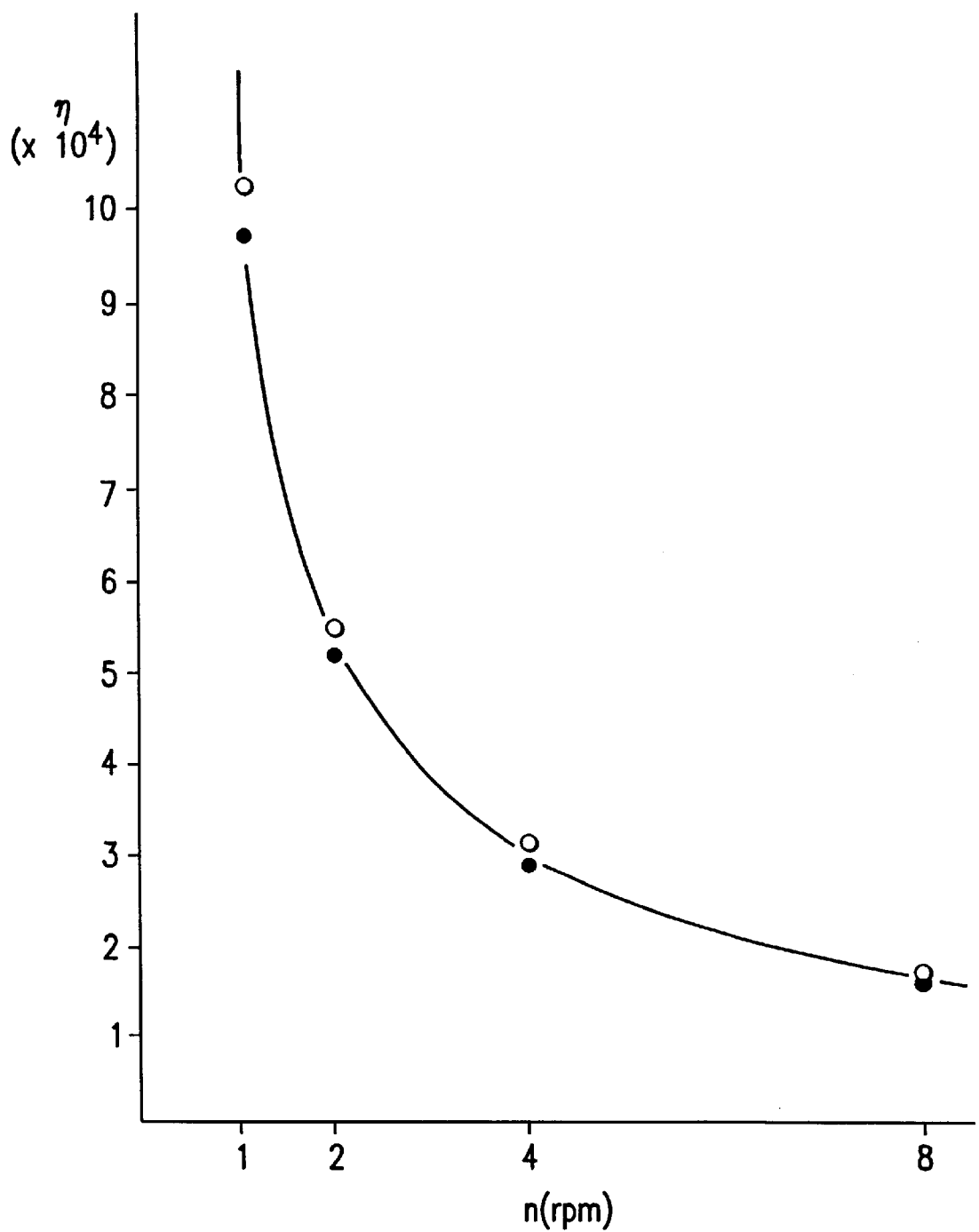
FIG. 1 is a graph of viscosity, $\mu$, in cps from 10,000–100,000, shown for convenience as $1-10 \times 10^4$, versus shear rate, n, in rpm for two separately made moisturizing compositions.

The present invention provides compositions comprising a polyelectrolytic bioadhesive pH buffering polymer and the use of the composition to institute and maintain an acid pH in the vagina, thereby inhibiting the growth of microorganisms causing bacterial vaginosis and the offensive odor associated therewith. The aqueous compositions of the present invention comprise an effective amount of a pH buffering polymer, and preferably, a water-soluble or water-dispersible, polymeric consistency enhancing agent. They are distinguished from the inventions disclosed in U.S. Pat. No. 4,615,697 and PCT/US89/00451 in that they do not contain a treating agent.

The pH buffering polymer is a bioadhesive polymer that is water-insoluble but water-swellable. The term water-insoluble as used herein means that the pH buffering polymer (lacking water-soluble impurities) is less than 1% soluble in water and shows no appreciable viscosity in its acid form at about pH 3 to 5 in a concentration no greater than about 2 to about 3% by weight. The term water-swellable means that the polymer, while not water-soluble, absorbs an appreciable amount of water, typically about 60 to about 100 times its dry weight. The composition is substantially non-toxic to mammalian tissues.

The pH buffering composition is designed for use on luminal vaginal mucosal cells of a mammal to which the composition adheres in the presence of a sufficient amount of water to swell the bioadhesive. In situ, the adhered composition buffers the contacted tissue for relatively long periods of time. Indeed, for buffering of vaginal cells, the pH buffering bioadhesive polymer can remain in place and active for a time period from about 48 to about 72 hours, i.e., the turn-over time for vaginal mucosal tissue.

The method of the present invention utilizes the pH buffering bioadhesive polymer in a hydrogel composition that holds substantial quantities of water in contact with the vaginal area of the host mammal for extended periods of time. The attachment of the bioadhesive polymer to the vaginal lining is via hydrogen bond formation involving the free carboxyl groups of the polymer. This results in both a bioadhesive affect and a polyelectrolytic affect, because both the oxygens and hydrogens of the carboxyl groups of the polymer and the hydrophilic groups of the cells in the vaginal mucosal lining (i.e., carboxy and hydroxy groups), through a resonance mechanism, allow for hydrogen bonding with the mucosal lining, as well as for the acidic hydrogens of the polymer to disassociate. The disassociated hydrogens first act to lower the pH of the vagina and the polyelectrolytic polymer then acts as a buffer to maintain the pH at this lower level. This effect is possible because of the relatively large supply of acidic hydrogens available and the relatively large size of the polymer, which allows for a ready distribution of charge when the acidic hydrogens disassociate from the polymer.

In accordance with this method of pH buffering, a composition containing water, a pH buffering effective amount of the pH buffering bioadhesive polymer and, preferably, a thickening-smoothening amount of a water-dispersible polymeric consistency-enhancing agent is provided, as described before.

The contact between the composition and vaginal mucosa is carried out in the presence of sufficient water to swell the buffering polymer and cause the buffer-containing composition to adhere to the area contacted. That contact is maintained for a period of time sufficient to lower the pH of the contacted vaginal cells, and adjoining tissues if desired, and maintain this lowered pH so as to control and reduce the growth of the organisms causing vaginosis. The mean vaginal pH observed for women treated with the bioadhesive composition of this invention was about 4.8, and was maintained for about 48 hours after treatment ended. In contrast the mean vaginal pH of untreated women was 5.6. The maintenance of such a lowered pH for up to 2 days post treatment indicates that daily treatment is generally not required. Thus, the composition provides for long-acting effectiveness against growth of the bacteria causing vaginosis.

In addition to keeping the growth of certain bacteria in check, an acidic pH, which is normally maintained by the lactobacilli of the vagina, also checks the growth of common yeasts, fungi and other microbes that cause vaginal infections which do not grow well at a pH of 5 or lower. As a further consequence, the pH buffering method of the present invention thus provides an added benefit in that it may also provide a method of inhibiting yeast and fungal growth as well as inhibiting bacterial infections in the vagina.

By keeping the growth of the bacteria in the vagina that cause vaginosis in check, the by-products produced by such organisms, including volatile amines, which are known to have a "fishy" smell, are also reduced. Moreover, it is believed that an acidic environment causes the odor-producing amines to be protonated, and thereby stabilized in a non-odoriferous amide form, or at least their release impeded, further eliminating vaginal odor. This elimination of odor is accomplished without the use of antibiotics, which, as discussed above, often causes unwanted side effects.

The buffering composition of the present invention also restricts ion efflux from the contacted vaginal mucous membrane. Such ion efflux, with its associated water, can cause water to move out of tissues. Further, as noted in co-pending U.S. patent application Ser. No. 732,738, the presently contemplated pH buffering bioadhesive produces a Donnan equilibrium effect, which facilitates ion influx into the contacted tissue. The bioadhesive properties of the composition allows for extended contact with the vaginal mucosa to provide moisturization of the contacted tissue. The moisturizing effects of the present composition, however, are secondary to its pH buffering effect. Thus, the present composition is meant to be used primarily by pre-menopausal women who do not require moisturization.

Generally, a lesser amount of the present buffering bioadhesive composition is required for maintaining a lowered pH than for providing vaginal moisturization. Applicants note the disclosure of Zinny and Lee (discussed above) wherein women where given doses of 2.5 g of a composition containing 2.0 weight percent bioadhesive polymer (REPLENS®). However, in that study, which was conducted with postmenopausal women, the composition was intended to provide vaginal moisturization as well as vaginal pH reduction. Additionally, as noted above, postmenopausal women have a relatively high normal vaginal pH and lack lactobacilli. Herein, the major aspect of the invention is to provide pH reduction so as to provide relief from infection and concomitant odor, not to provide moisturization to those who experience vaginal dryness, i.e., postmenopausal women.

In accordance with the invention, the pH buffering composition may be administered via several means to provide the desired contact with vaginal epithelial cells. For example, the composition may be applied by rubbing the composition over the area to be moisturized. Alternatively, the composition may be applied by spray, hand, forceps, suppository, plunger, douche or other suitable instrument.

The composition is left in situ (contact maintained) for a time that is sufficient to first lower the vaginal pH and then to continue to buffer the vagina to maintain the lower pH. Generally, several applications are required to provide a full therapeutic benefit. Following administration, the composition is eliminated from the body by a natural bodily mechanism, such as by dispersion or erosion caused mechanically or by an aqueous body fluid such as vaginal secretions, or by washing or douching. The pH buffering composition may also be removed by mechanical action at the site of contact. Because of its bioadhesive properties, the pH buffering polymer remains in the vagina for at least approximately 10 hours up to approximately 3 days, in contrast to previous topically applied vaginal treatments, which are cleared from the vagina within 30–90 minutes.

As provided herein, the principal component of the pH buffering composition of the present invention is the bioadhesive polymer. In addition to the bioadhesive polymer, the composition also contains water and, preferably, a water-dispersible consistency-enhancing agent. Lactoadjuvants or diluents may also be present, as well as other ingredients that are known for use in similar compositions.

The bioadhesive polymer comprises a water-swellable, but water-insoluble, cross-linked carboxy-functional polymer that exhibits bioadhesion as discussed below. The polymer preferably contains a plurality of monomers, of which at least about 80 percent contain at least one carboxyl functionality [—COOH] and a cross-linking agent, in an amount such that the polymer is water-swellable but water-insoluble. Preferably, at least about 90 percent of the monomers contain at least one carboxyl functionality, still more preferably, at least 95 percent of those monomers contain at least one carboxyl functionality. Also in most preferred practice, the bioadhesive contains about 0.05 to about 2 percent by weight cross-linking agent, although it may contain about 0.01 to about 10 percent by weight cross-linking agent.

A bioadhesive may be defined as a material that adheres to live or freshly killed biological surface, such as mucous membrane or skin tissue. "Bioadhesion", as used herein to define a useful bioadhesive pH buffering polymer, is assayed by the procedure described in U.S. Pat. No. 4,615,697, incorporated herein by reference, that measures the force required to separate two layers of freshly excised rabbit stomach tissue that are adhered together by an adhesive.

For purposes of the present invention, a bioadhesive is defined as a material that requires a force of at least about 50 dynes/cm$^2$ to separate two freshly excised pieces of rabbit stomach tissue adhered to one another by means of the bioadhesive. More preferably, the force is at least about 380 dynes/cm$^2$. An average force observed for polycarbophil, a preferred bioadhesive polymer, in the practice of the present invention, is about 1073 dynes/cm$^2$. Upper limits for forces required to separate the freshly excised rabbit tissue are presently unknown, but are believed to be at least about 2000 dynes/cm$^2$.

As noted previously, preferably at least about 80 percent of the monomers of the preferred bioadhesive polymer contain at least one carboxyl functionality [—COOH] which is necessary to achieve the desired amount of water-swellability in the water-insoluble polymer and for bioadhesion. Monomers for use herein include those that are mono-unsaturated, triple-bonded carbon-carbon linkages, i.e., an ethylene linkage [C≡C], such as acrylic acid, methacrylic acid, fumaric acid, maleic acid, maleic anhydride which may be hydrolyzed into its acid form during or after polymerization, itaconic acid, crotonic acid, and the like. Each of these acids can be used alone or in combination with other such acids or with one or more pharmaceutically or cosmetically acceptable salts of those acids. Acrylic acid is a particularly preferred monomer for providing the carboxyl groups of the bioadhesive polymer.

A preferred bioadhesive polymer useful in this invention is cross-linked by a cross-linking agent as is known in the art. Exemplary useful cross-linking agents include divinylbenzene, N,N-diallylacrylamide, 3,4-dihydroxy-1,5-hexadiene, 2,5-dimethyl-1,5-hexadiene and the like.

The amount of added cross-linking agent is of some importance. When less than about 0.05 weight percent of an appropriate cross-linking agent is added to the monomers, the pH buffering polymer so formed tends to become water-soluble, or water-dispersible, thereby losing its desired water-insoluble, water-swellable, character that is important to the invention. When greater than about 1 or 2 percent cross-linking agent is added, depending on the polymer, the water-swellability of the bioadhesive begins to decrease appreciably. This is particularly so for divinylbenzene or dihydroxy- or dimethyl-substituted hexadiene cross-linking agents. Preferably, the cross-linking agent is added at about 0.05 to about 1 or 2 weight percent of the monomers. However, the preferred range will vary, inter alia, with the nature of the polymer, the nature of the cross-linking agent and the degree of cross-linking. The important aspect of the amount of cross-linking agent to be added is that the amount added should ensure that the polymer is water-insoluble but water-swellable which is well within the skill of the average practitioner in the art to determine the optimum amount for a given application, without undue experimentation.

A bioadhesive polymer useful herein can thus, in part, be defined as a reaction product of the copolymerization of at least 80 weight percent monoethylenically unsaturated carboxy-functional monomer to which has been added about 0.01 to about 2.0 weight percent of a cross-linking agent. The remaining monomers that can be present to constitute 100 percent by weight of the monomers are discussed below.

The pH buffering polymer can also include, at less than about twenty percent of the total monomer units polymerized, monoethylenically unsaturated monomers such as $C_1$–$C_6$ alkyl esters of one or more of the above-described acids such as hexyl acrylate, butyl methacrylate and methyl crotonate; hydroxyalkylene-functional esters of the above-described acids that contain, per molecule, an average of 1 to about 4 oxyalkylene groups containing 2–3 carbon atoms such as hydroxyethyl methacrylate, hydroxypropyl acrylate and 5 tetraethylene glycol monoacrylate; methacrylamide, acrylamide and their $C_1$–$C_4$ mono- and di-alkyl derivatives, such as N-methyl acrylamide, N-butyl methacrylamide and N,N-dimethyl acrylamide; styrene; and the like as are known in the art as being copolymerizable with the above described carboxyl functionality-containing monomers and cross-linking agents. Most preferably, the bioadhesive polymers are prepared from only the monoethylenically unsaturated carboxy-functional monomer and the cross-linking agent.

A pH buffering moisturizing polymer useful herein can be prepared by conventional polymerization techniques described in the literature. Exemplary preparations of useful bioadhesives are provided hereinafter and can also be found in U.S. Pat. Nos. 2,810,716 and No. 3,202,577, incorporated herein by reference.

A polymer of this invention can also be prepared as described in European Patent publication No. EP 0 301 532 A2, published Feb. 1, 1989. In accordance with that disclosure, acrylic acid and a cross-linking agent are reacted in carbon dioxide as solvent in the presence of an appropriate free radical initiator at a temperature of about 45° C. to about 65° C. and at a pressure above the mixture critical point, e.g., about 1250 pounds per square inch at 45° C. to provide a fine, fluffy polymer.

As noted, the pH buffering polymers useful herein are swellable, but insoluble, in water. Reference to the properties of the pH buffering polymers of this invention as being swellable, but insoluble, in water, means that the polymers can absorb water, typically about 1 to about 100 times their weight in water but are sufficiently insoluble to provide a measurable viscosity at pH 6.5 at a concentration of 0.2 percent by weight in water.

The bioadhesive polymers of this invention are swellable in water, i.e., the polymer particles sorb water (adsorb or absorb) and thereby become larger in size in the presence of water. The water used for such swelling is, typically, that provided by the aqueous composition of the present invention or it can, in part, be water that comes from tissues of the treated animal, such as by moisture transpiration or secretion through the skin, by mucosal transpiration in secretions, such as here, vaginal mucosal secretions. See, also, the discussion of the Donnan equilibrium effect of the polymers above.

The size of the bioadhesive particles has an effect upon the compositions of this invention. The bioadhesive particles should not be so large that the composition cannot be administered without undue difficulty. Similarly, particles sized larger than those discussed below can sometimes cause pain and irritation when administered for vaginal use. In addition, it is believed that particles sized as discussed below provide an improved functioning to the buffering composition as compared to particles that are larger in size, i.e., in the longest dimension.

Typically, at the maximum, a useful bioadhesive polymer is sized to pass through a No. 400 sieve screen (U.S. Standard Sieve Series), i.e., a 38 micron opening. Preferably, the bioadhesive polymer particles for use in the composition of the invention are smaller, e.g., sized so that the longest dimension is no greater than about 20 microns. Most preferably, the particles have a number average size of about 2 microns to about 5 microns in the longest dimension. Particles of a desired size are obtainable, for example, by grinding, crushing or otherwise comminuting larger particles, as well as by direct polymerization.

Particles having a relatively small size have a greater surface area per unit weight, swell more rapidly, and appear to adhere better than do particles having a relatively large size, and thus, a relatively small size is preferred for the particles. Bioadhesion measurements discussed above are carried out for convenience using a bioadhesive sized to pass through a No. 300 sieve screen and be retained on a No. 400 sieve screen (U.S. Standard Sieve Series), i.e., a No. 300/400 sized particle.

Bioadhesion has not been found to be a function of the molecular weight of the bioadhesive. Consequently, the bioadhesive can be of substantially any molecular weight, so long as its adhesion in the adhesion test described below is at least about 50 dynes/cm$^2$ and preferably about 380 dynes/cm$^2$.

As noted previously, the bioadhesive polymers can be prepared by polymerization in an aqueous medium. In preferred practice, the aqueous medium is a saturated solution of an alkaline earth metal salt, such as magnesium sulfate, which serves at least two functions. First, it increases the density of the polymerization medium so that the polymerized bioadhesive floats on the surface of the aqueous medium and can be easily removed therefrom. Second, the use of the alkaline earth metal salt, in particular magnesium sulfate, reduces the swelling of the bioadhesive in the aqueous medium so that polymerization and recovery are facilitated.

Bioadhesives so prepared typically contain about 0.5 to about 1 percent of the alkaline earth metal ion after rinsing the polymer several times in water to remove the earth metal salts used in the preparation of the polymer. These polymers thus differ from those polymers in which an alkaline earth metal hydroxide is used to neutralize the carboxyl groups, to produce a salt of the polymer such as calcium or magnesium polycarbophil. These neutralized polymers do not contain the hydrogens that are necessary to function as a pH buffer or bioadhesive and are not contemplated as useful in the invention herein.

Particularly preferred bioadhesives for use in the present invention are the commercially available materials sold under the designation polycarbophil by A. H. Robins Co. of Richmond, Virginia, and CARBOPOL® "EX55" also known as CARBOPOL® 976 and NOVEON All® by B. F. Goodrich Chemical Co. of Cleveland, Ohio, the manufacturer of CARBOPOL® 934 that is also discussed herein. *The United States Pharmacopeia* (U.S.P.) 1980 ed., United States Pharmacopeial Convention, Inc., Rockville, Md., at page 638, defines polycarbophil as a polyacrylic acid cross-linked with divinyl glycol that has a residue on ignition of less than 4.0 percent and in water absorbs about 60 times its original weight, in test B under Absorbing power. The 1985 edition of the U.S.P. lists only calcium polycarbophil that contains 18–22 percent calcium and is different from the material described in the 1980 edition.

The material designated as "EX55" from B. F. Goodrich Co., above, has a specific gravity of about 1.4 and sorbs (absorbs and adsorbs) about 60 to about 100 times its weight of water. That sorption value is similar to the sorption capacity of natural mucin. In contrast, CARBOPOL® 934 is reported to sorb several hundred times its weight of water. A useful bioadhesive is also a polyanionic polymer with a charge density similar to mucin.

Bioadhesive polymers useful in the practice of the present invention were examined as to their densities, which are typically about 1.30–1.70 grams/cubic centimeter (g/cc), or a specific gravity of about 1.30–1.70. The cross-linking percentage was found to have a small effect upon the resulting density of illustrative, synthesized polymers.

The pH buffering bioadhesive polymer is present in the compositions of the present invention in an amount that is sufficient to induce a lower vaginal pH and to buffer the vagina at this lower pH for a desired period of time. Such an amount is referred to herein as "an effective pH buffering amount". It is well known that effective amounts of active agents vary with the particular agent employed, the condition being treated, the degree of infection, the intensity of symptom, and the rate at which the composition containing the agent is eliminated from the body, as well as varying with the animal in which it is used. Consequently, specific effective amounts of pH buffering agents cannot be defined for each agent, but can be determined by those skilled in the art with relative ease and without undue experimentation.

Thus, an effective pH buffer amount is that amount, which in a composition of the present invention, provides a sufficient amount of hydrogens to induce and maintain the requisite pH in the vagina of the treated mammal for the desired period of time. An effective amount can therefore also be defined as an effective pH buffering amount.

A pH buffering composition utilized in the method of the present invention contains about 0.25 grams to about 15 grams (g) of bioadhesive polymer per 100 milliliters of the total composition (i.e., about 0.25 to about 15 weight percent). More preferably, the bioadhesive polymer is present at about 2 to about 5 grams per 100 ml of composition (about 2 to about 5 weight percent).

The water of the composition can be provided by the composition or by the contacted vaginal mucosa, or both. Thus, the bioadhesive buffering agent can be dispersed and pre-swollen in an aqueous medium prior to application, or can be applied dry and free of water or can be applied dispersed in a vehicle that contains enough water to partially hydrate the particles of the bioadhesive polymer.

Compositions of the present invention preferably also contain a thickening-smoothening amount of a consistency-enhancing agent, i.e., a water-soluble or water-dispersible polymer. A consistency-enhancing agent useful herein possesses sufficient water-solubility or water-dispersibility such that even small amounts can radically alter the viscosity of an aqueous composition. Such materials can exhibit bioadhesion, but because of their solubility or dispersibility in aqueous media, they tend to be lost relatively quickly from a composition and thereby do not provide the relatively long term pH buffering effect that is provided by the bioadhesive polymer discussed above. A consistency enhancing agent will generally be referred to herein as being water-dispersible.

Regardless of whether a consistency-enhancing agent is dispersed or truly dissolved, a composition containing such an agent present at up to about 10 percent in deionized or distilled water forms a single phase to the naked eye at 20° C. and, once prepared, does not exhibit separation when maintained at 20° C. for 24 hours. Where the consistency-enhancing agent is an acid, cations such as sodium, potassium and ammonium ions that are utilized to disperse or dissolve the consistency-enhancing agent can also be present in the composition.

Exemplary consistency-enhancing agents include anionic (carboxyl group-containing) and non-ionic polymers such as those containing a plurality of carboxyl groups and those containing a plurality of $C_2$–$C_3$ hydroxyalkyl groups. Preferred consistency-enhancing polymer agents include carboxymethyl cellulose, hydroxypropyl cellulose, hydroxyethyl starch derivatives, hydroxyethyl cellulose, gums such as tragacanth, hydroxyethylacrylate or methacrylate, polyacrylamide, and lightly cross-linked polyacrylic acid polymers like the before-described CARBOPOL® 934, which is particularly preferred. CARBOPOL® 934 is reported by the manufacturer, B. F. Goodrich, to be a polymer of acrylic acid that is cross-linked with polyallyl sucrose (a polyalkenyl sucrose) containing an average of at least three allyl groups per molecule. The preferred consistency-enhancing agent polymers are thus seen to be derivatized polysaccharides and polyacrylic acids, i.e., amides and hydroxyethyl esters. Additional consistency-enhancing polymer agents include polyvinyl pyrrolidone, polyvinyl alcohol and polyethylene oxide.

A consistency-enhancing agent functions in a composition described herein as its name implies, i.e., to enhance the consistency of the composition. That enhancement is in two areas: viscosity and texture.

As previously noted, a consistency-enhancing agent useful herein is water-dispersible and a relatively small amount of such a material can greatly increase the viscosity of or thicken an aqueous composition. Inasmuch as the bioadhesive polymer provides relatively poorly controlled viscosity-building effects to an aqueous composition, a composition containing only a pH buffering bioadhesive polymer can be too thin and runny or too stiff for a suitable vaginal product.

When admixed in the amounts and under the conditions discussed below, a bioadhesive pH buffering polymer and a consistency-enhancing polymer combine to provide an appropriately thickened aqueous pH buffering composition useful for vaginal application.

A particularly unexpected effect of the admixture of a useful pH buffering bioadhesive polymer and a consistency-enhancing polymer agent is that the texture of the resulting thickened composition is made smoother than when a bioadhesive polymer is utilized alone. Thus, an aqueous composition that contains only a pH buffering bioadhesive polymer can exhibit a stiff and almost gritty feel and, as such, could be uncomfortable in a vaginal product, particularly if present during intercourse.

On the other hand, the presence of a consistency-enhancing polymer agent unexpectedly smoothens the aqueous composition such that it exhibits substantially no stiffness or grittiness. The smoothening of texture also provides enhanced lubricity to the composition.

The use of a single amount of the consistency-enhancing polymer agent provides both the required thickening and smoothening. Thus, the amount of the material utilized is described as a thickening-smoothening amount. The consistency-enhancing agent can be a single polymer or mixture of polymers such as those discussed above.

The consistency-enhancing polymer agent is present in a thickening-smoothening amount, which, along with the other components that may be present in the composition preferably provides a gel-like consistency with a viscosity of the product of about 4,000 to about 100,000 cps at 25° C., measured as provided below. As provided in greater detail below, the viscosity of the composition is a function of several variables, each of which can be changed to alter or maintain a desired viscosity.

A typical composition can contain about 0.25 to about 10 weight percent of a consistency-enhancing agent polymer. More particularly, an amount of about 0.5 weight percent to about 5 weight percent is utilized.

A greater amount of a consistency-enhancing agent is generally utilized with a smaller amount of bioadhesive polymer, and vice versa. For example, a composition at a pH value of 2.2–2.5 containing 0.25 weight percent polycarbophil as the bioadhesive requires about 8–10 weight percent CARBOPOL® 934 to achieve a viscosity appropriate for mechanical placement in the vagina.

The water of the composition can be provided in the composition or by the contacted vaginal cells, or both, although typically, the water is provided by the composition. Thus, the pH buffering bioadhesive and preferably consistency-enhancing agents are admixed and pre-swollen in an aqueous medium prior to application, or can be applied admixed in an aqueous vehicle that contains enough water to partially hydrate the bioadhesive buffering agent particles and the consistency-enhancing agent.

A useful pH buffering aqueous composition of the present invention has at room temperature a consistency of a barely pourable liquid to a gel, the latter being preferred, with the consistency being a function of relative amounts of water, pH buffering bioadhesive polymer, consistency-enhancing polymer agent (when present), osmoticity and the pH value of the composition formed. A relatively low amount of the polymers in a given amount of water produces a relatively thinner composition than does a greater amount of the polymers, with the pH value being held constant at both concentrations.

The $PK_a$ of a useful pH buffering bioadhesive polymer is about 3 to 5, with a preferred polymer, polycarbophil, having a $PK_a$ of about 4.5. As a consequence, where a composition is at a pH value of greater than 5, substantially all of the acidic protons (hydrogens) are neutralized and the polymer-containing composition exhibits its thickest consistency for that concentration. On the other hand, at pH values such as 2, well below the $PK_a$ value of the polymer, the composition is relatively thinner, for a given concentration. Moreover, a composition that might irritate the vaginal tissue when applied, as might occur if the composition had a pH of about 2, is not favored. However, the pH of the composition should be more acidic than the vagina, which when infected has a pH of between about 5 and 6, so as to be able to lower the pH of the vagina to stimulate growth of beneficial lactobacilli as well as inhibit detrimental microorganism growth and prevent and/or stop vaginal odor.

The $PK_a$ values for the consistency-enhancing agents such as the particularly preferred CARBOPOL® 934 are similar to that of the bioadhesive polymer. As a consequence, use of a composition at a pH value of about 5 or greater provides the thickest composition, whereas a pH value of about 2 provides the thinnest composition, for a given concentration of consistency-enhancing agent, all other components being held constant. However, non-ionic consistency-enhancing agents have less of a change in viscosity (and, hence, that of the composition) over a pH range than do anionic agents.

In addition, osmoticity of a composition can also play a role in the viscosity of the composition. Typically, higher solute concentrations decrease the viscosity of the composition when the amounts of bioadhesive polymer, consistency-enhancing polymer (when present), water and the pH value are kept constant. Thus, the viscosity of a composition having a pH greater than 5 can be reduced from that of a ringing gel (that is, like JELL-O®, it rings or vibrates when tapped) to a pourable liquid by increasing the osmoticity of the composition.

An isotonic product has an osmoticity of about 280 to about 320 mOsM, measured by use of a vapor phase osmometer, and such an osmoticity is generally useful herein. The osmoticity of the composition according to the present invention, however, can be as high as about 450 to about 500 mOsM.

Pharmaceutically acceptable electrolytes and nonelectrolytes (collectively referred to as solutes) are used for adjusting osmoticity and viscosity of the compositions useful for vaginal pH control. Exemplary pharmaceutically acceptable electrolytes include sodium or potassium chloride, mono-sodium or mono-potassium phosphate, di-sodium or di-potassium sulfate, and sodium or potassium bicarbonates. However, electrolytes which would neutralize the polymer, e.g., hydroxides, should not be used. Exemplary pharmaceutically acceptable non-electrolytes useful as solutes include glycerin, sugars such as glucose and sucrose, sorbitol and urea. Thus, those solutes that are well known for adjusting osmolarity or osmolality are useful herein.

Thus, compositions containing a pH buffering bioadhesive polymer with or without a consistency-enhancing polymer agent at or near the high end of the aforementioned concentrations of consistency enhancing agent and at a pH value of about 5 or greater exhibits more gel-like properties. Such compositions can, nevertheless, be extruded in the form of drops, e.g., from an eye dropper or live device, particularly where sufficient electrolyte or other solute is present to raise the osmoticity to near about 450 mOsM. Conversely, compositions at or near the low end of the aforementioned concentrations of consistency enhancing agents and at a pH value below about 3 typically behave as barely pourable liquids, unless a large amount of bioadhesive polymer is present.

For example, compositions for vaginal moisturization exhibit a viscosity of about 4,000 to about 100,000 cps at 25° C. The thicker compositions typically exhibit non-Newtonian flow characteristics. The viscosity of such solutions is therefore measured with a viscometer that is especially designed for such compositions, such as the commercially available Haake ROTOVISCO Model RV-12, available from Haake, Inc., 244 Saddle Brook Road, Saddle Brook, N.J. 07662. The machine utilizes an SV cup and an SVII rotor for determining viscosity in centipoises (cps) at shear rates of 1–8 revolutions per minute (rpm) and at a temperature of 25° C.

With the extremes of consistency and pH in mind, a worker of ordinary skill can readily formulate a pH buffering composition having a desired consistency and pH without undue experimentation. It should also be understood that the pH value of a pH buffering composition can change once the composition is contacted with the vaginal tissues as a result of the local pH value of the area to which the composition is applied and the secretions of the vagina. However, it should be noted that the greater the amount of buffer added to the vagina, the less the pH of said composition will change since the buffer will not be consumed as readily and this is a factor in determining what may be an effective amount for a given application.

The pH buffering composition is applied to the vaginal surface in an amount sufficient to form a layer of hydrated bioadhesive particles that is substantially continuous over the applied surface. Typically, that layer is several particles thick. In terms of dry pH buffering bioadhesive polymer, the polymer is applied in an amount of about 0.05 to about 3.0 milligrams (mg) per square centimeter ($cm^2$) of contacted vagina cells. Given that the vagina of an average size woman has an interior surface area of approximately 40 $cm^2$, a dosage of about 1.75 grams of a gel according to the present invention containing 2% by weight of polyelectrolytic polymer has been found to be therapeutically efficacious. Application to the vaginal epithelia can be, and preferably is, in excess of that needed to provide buffering.

In addition to the pH buffering bioadhesive polymer agent and consistency-enhancing agent, compositions useful in the present invention can also contain one or more pharmaceutically or cosmetically acceptable additives that are referred to herein as adjuvants that typically assist in providing extended shelf life and customer acceptance of a hygiene product. Exemplary adjuvants include preservatives, tissue toners, tissue conditioning agents, tissue feel enhancers, emollients, lubricating oils (e.g., lipids), emulsifying agents, humectants, coloring agents, and odor providing agents (odorants).

Typical preservatives known for use with feminine hygiene products include alcohol, ascorbyl palmitate, benzoic acid, butylated hydroxyanisole, butylated hydroxytoluene, chlorobutanol, ethylenediamine, ethylparaben, ethyl vanillin, glycerin, methylparaben, monothioglycerol, phenol, phenylethyl alcohol, phenylmercuric nitrate, propylparaben, sassafras oil, sodium benzoate, sodium formaldehyde sulfoxylate, sodium metabisulfite, sorbic acid, sulfur dioxide, maleic acid, and propyl gallate. Obviously, to the extent any of the foregoing preservatives are irritating to the vagina, less irritating preservatives should be chosen.

Typical emollients known for use with feminine hygiene products, which are useful herein, are generally bland, fatty or oleaginous substances including castor oil, sulfated castor oil, cocoa butter, coconut oil, cold cream, corn oil, cottonseed oil, rosewater ointment (also known as cold cream), combinations of white wax and white petrolatum, combinations of sodium lauryl sulfate, propelyne glycol and stearyl alcohol, sesame oil, theobroma oil, myristyl alcohol and shark liver oil.

Typical lubricating agents or oils known for use with feminine hygiene products, which are useful herein, are petrolatum, white or yellow wax, coca butter, oleic acid, olive oil, jojoba oil, paraffin, starch glycerite, lanolin, hydrophilic petrolatum, mineral oil, cetyl alcohol, glyceryl monostearate, stearic acid, polyethylene glycols, polyoxyl 40 stearate, polysorbate, cholesterol and higher molecular weight lipids.

Emollients and lubricants provide hygiene products with the appropriate slip, tactile feel and rub-in properties to enhance the ease of usage and to encourage the consumer to use the product more liberally and more frequently. Certain quaternary compounds allow substances like petrolatum to be combined with glycerine and in personal-care products without feeling greasy. The petrolatum-glycerine combination is especially effective in alleviating dry skin.

Typical emulsifying agents known for use with feminine hygiene products, which are useful herein, are sodium alginate, carbomer, sodium carboxymethylcellulose, carrageenan, gelatin, hydroxyethylcellulose, hydroxypropylcellulose, hydroxypropylmethylcellulose, octoxynol-9, oleyl alcohol, polyvinyl alcohol, povidone, sodium lauryl sulfate, sorbitan esters, stearyl alcohol, tragacanth, and xanthan gum. Emulsifying agents are used to produce oil-in-water emulsions and can be classified into three types: monomolecular, multimolecular and solid particle. Known monomolecular emulsifying agents include potassium laurate, polyoxyethylene sorbitan monooleate. Multimolecular emulsifying agents include acacia and gelatin. Solid particle emulsifying agents include bentonite, graphite and magnesium hydroxide. Emulsifying agents can also be classified chemically into anionic, cationic and nonionic.

Typical humectants known for use with feminine hygiene product agents, which are useful herein, are glycerin, propylene glycol, pyrrolidone carboxylic acid, sodium lactate, urea, and certain natural lipid mixtures. Other known humectants include certain proteins, gelatin, hyaluronic acid, vitamins and some natural ingredients. Some of the proteins used are collagen, elastin, placental proteins and proteins from epidermal tissues of mammals are also used.

The preparations are rendered sterile by autoclaving at elevated temperatures and pressures for a sufficient level and for a sufficient time to kill all bacterial contaminants or they are prepared under aseptic conditions. The preparation is rendered pyrogen-free by the use of pyrogen-free water which is available from commercial laboratories.

The phrases such as "pharmaceutically acceptable", "cosmetically acceptable" or "physiologically tolerable" are used herein to mean that the material so described can be used for treatments in or on humans or other mammals without causing ill effects, such as toxicity, blistering or whitening of mucosal tissues, and that those materials are not themselves bioadhesive pH buffering agents, as those words are used herein. Exemplary adjuvants can be found in Chapter 67 of *Remington's Pharmaceutical Science*, 16th ed., Osol, et al. eds., Mack Publishing Company, Easton, Pa. (1980), as well as in Chapter 84 of the Seventeenth Edition thereof.

It is noted that the above-mentioned adjuvants can be present in an amount that is greater than the bioadhesive polymer. Even though such may be the case, the adjuvants do not provide pH buffering capacity to the composition, but rather provide emulsification or lubricity or the like, and typically assist in application of the compositions. This is the case where a compound, such as glycerin or sorbitol, that is a known humectant is present, since such materials are water soluble, non-bioadhesives that are readily lost from the surface of the tissues. Lubricating oils and emulsifying agents provide lubricity to a composition that may be used during sexual intercourse.

A pH buffering composition useful herein can be applied to contact the vagina as a dry powder, an aqueous suspension or a non-aqueous suspension. The application can be in the form of a spray of the powder or a suspension, as drops, or as a composition having a cream or gel-like consistency.

In one embodiment, the dry pH buffering bioadhesive polymer is swollen in an aqueous medium at a desired pH value, and then applied to contact the desired tissue. The word "dry" is used herein in relation to a bioadhesive moisturizing polymer to mean that the dry polymer does not adhere when touched with a finger within a rubber glove, and is substantially unswollen.

The composition can also be formulated as suppositories for vaginal administration, in which case the bioadhesive polymer is dispersed therein. A thin aqueous dispersion of bioadhesive buffering particles is also useful as a vaginal douche. A gel-like consistency is preferred for a vaginal buffer, with the composition being applied by means of a squeeze-type applicator as is well known for use in applying vaginal products. See, e.g., U.K. Design Registration Ser. No. 2,016,550. Plunger-type applicators have also been found to be efficacious.

The following examples are meant to exemplify the present invention and should not be construed as limiting:

Example 1

One-hundred and thirty women were either given samples of 1.75 grams of a composition prepared in accordance with the present invention for three weeks and a placebo for three weeks to help relieve vaginal odors. The composition of the present invention that the women in the study were given comprised water (78.82%), polycarbophil (the pH buffering bioadhesive polymer) (2.00%), mineral oil (4.20%), glycerin (12.90%), carbomer 934P (the consistency-enhancing agent) (1.00%), hydrogenated palm oil glyceride (Myverol) (1.00%) and sorbic acid (0.08%). (All percentages are weight percents.) The composition of the present invention used herein had a pH of about 3.

The composition and placebo were applied twice weekly for the first two weeks of each three week cycle. The women were asked to record in a diary their satisfaction with the product. The women were divided into three subgroups according to their self-diagnosed smell, "vinegar", "sweat" or "fish", after the study was finished so as to better analyze the results.

Figure 2:
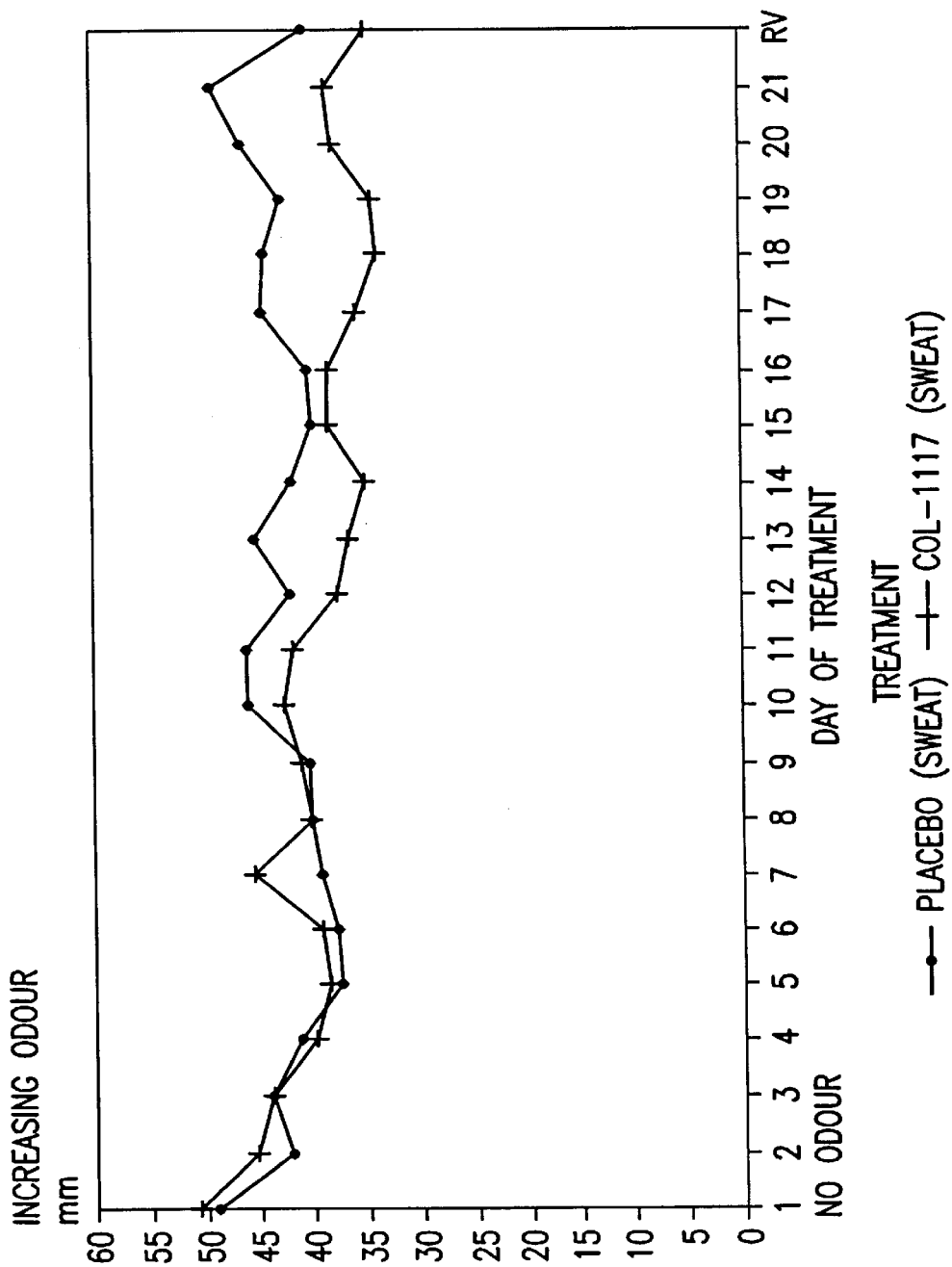
FIG. 2 is a graph comparing the reduction of a vaginal odor of "sweat" between women receiving a placebo and those receiving a composition of the present invention.
Figure 3:
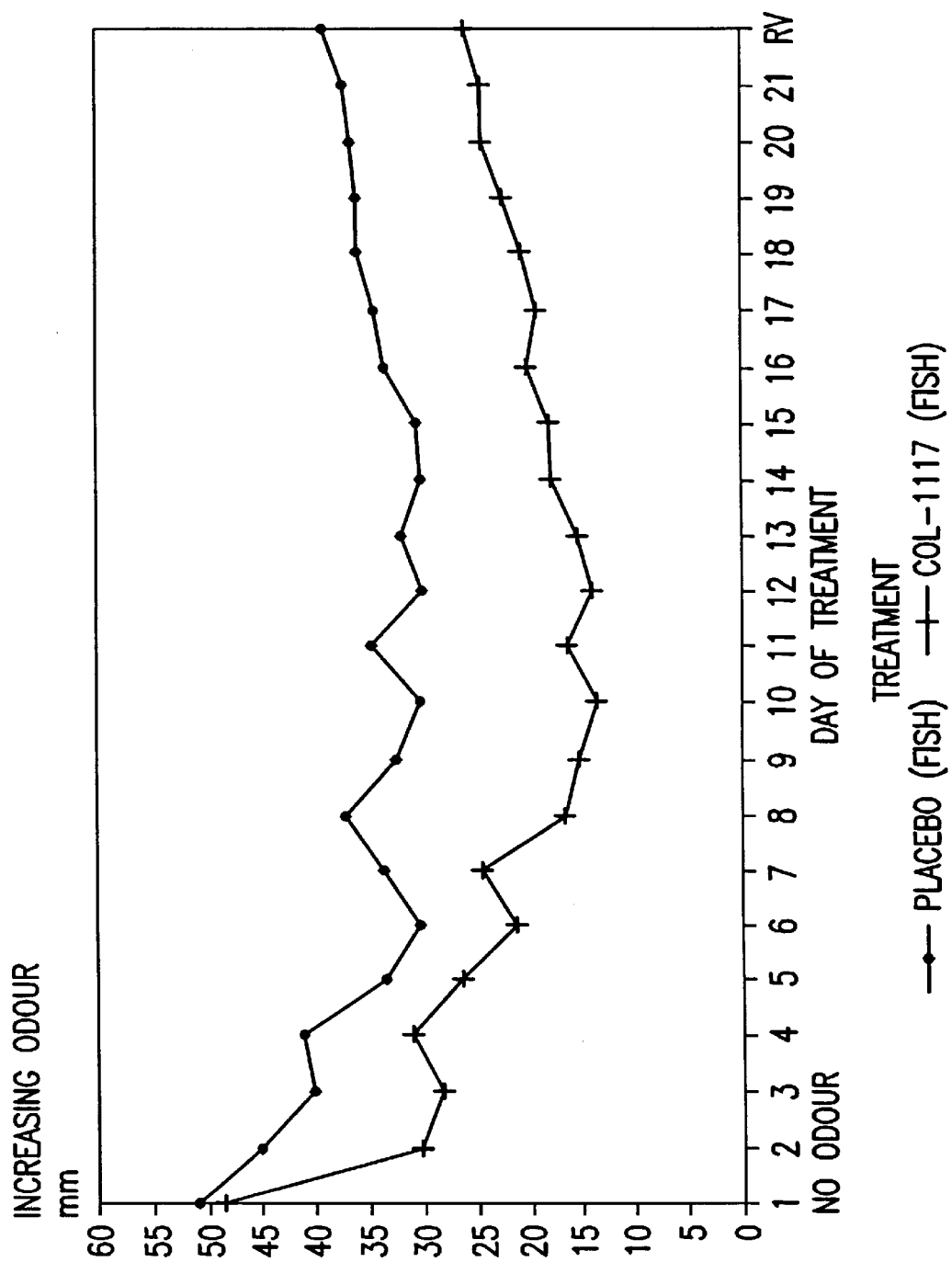
FIG. 3 is a graph comparing the reduction of a vaginal odor of "fish" between women receiving a placebo and those receiving a composition of the present invention.
Figure 4:
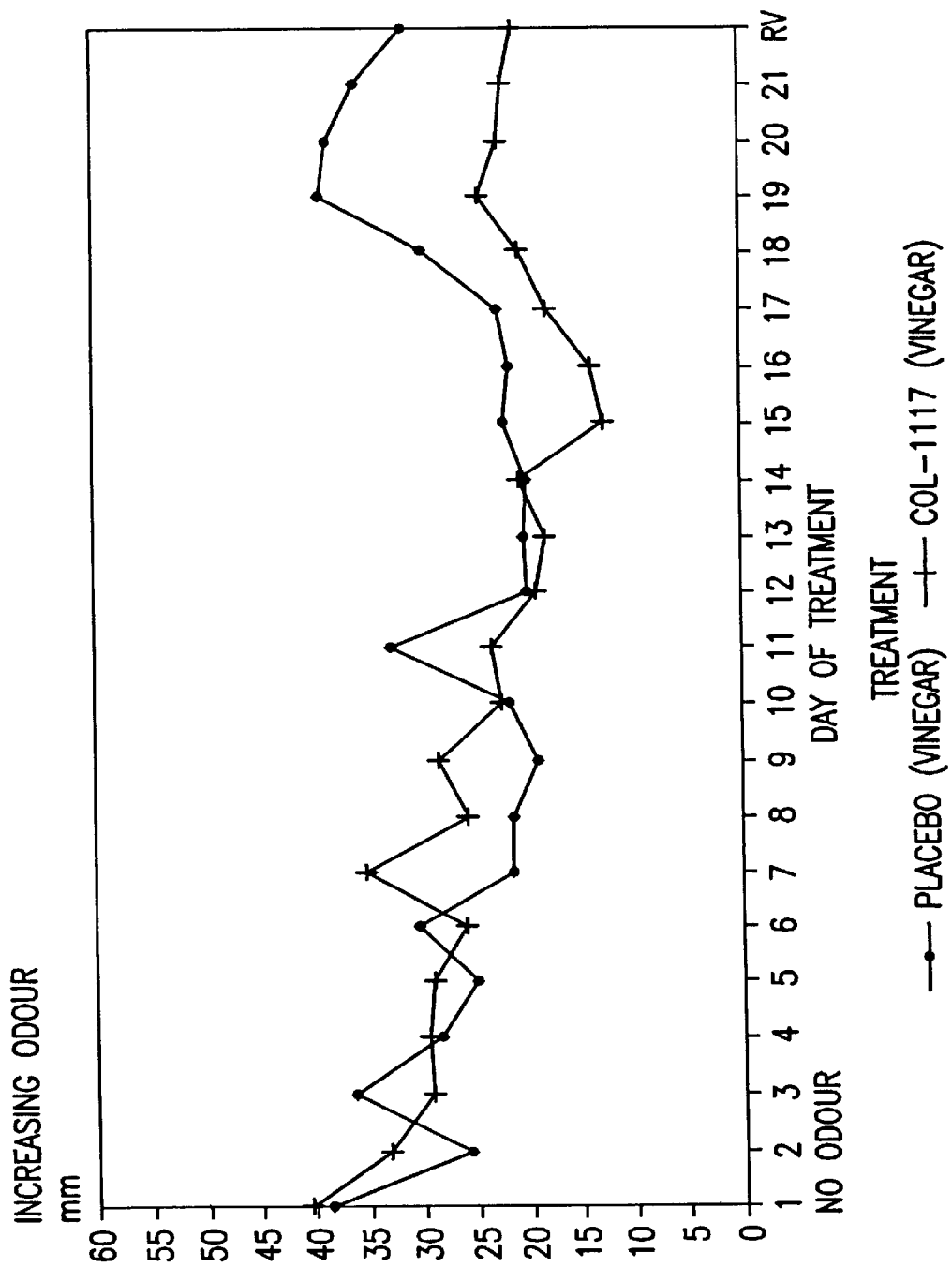
FIG. 4 is a graph comparing the reduction of a vaginal odor of "vinegar" between women receiving a placebo and those receiving a composition of the present invention.
Figure 5:
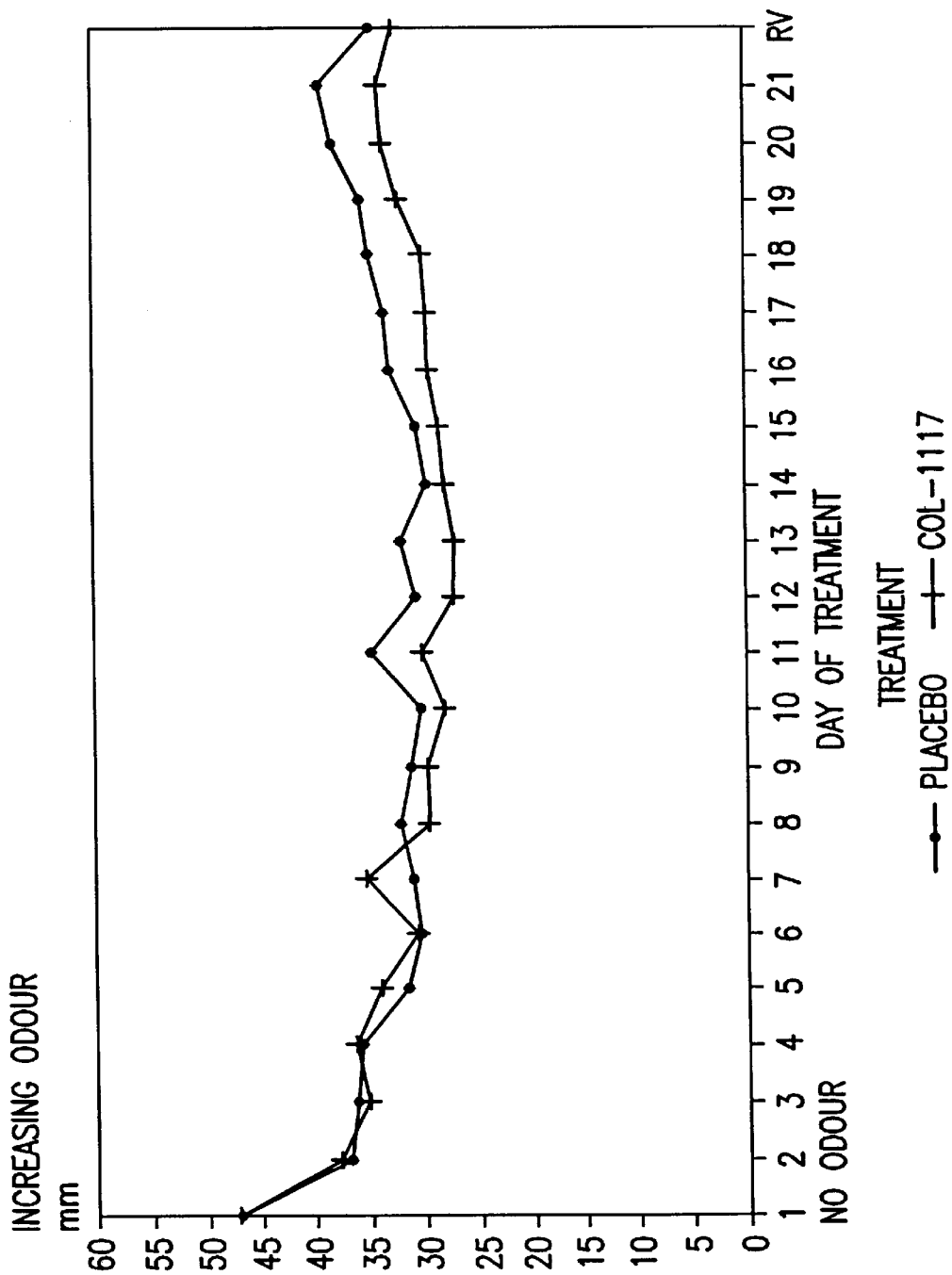
FIG. 5 is a graph comparing the reduction of all vaginal odors between women receiving a placebo and those receiving a composition of the present invention.

The results are summarized in FIGS. 2, 3, 4 and 5. FIG. 2 illustrates the results for women who were in the "sweat" subgroup, FIG. 3 illustrates the results for women who were in the "fish" subgroup, and FIG. 4 illustrates the results for women in the "vinegar" subgroup. FIG. 5 illustrates the results for all women. The composition was most effective for women in the "fish" subgroup, since the "fish" smell is probably caused by volatile amines thought to be produced by the anaerobic bacteria, including Mobiluncus, whose growth is checked by a low pH in the vagina. Additionally, a low pH also causes amine protonization, producing non-volatile salts, and thereby reduces the amine "fish" smell. It is unclear if the women in the other two subgroups actually had bacterial vaginosis and so the results of testing on these women was inconclusive.

Example 2

Ten women were given samples of compositions of the present invention, prepared substantially as described in Example 1. The women topically applied to the vagina daily doses of 2.5 grams of the composition for a period of one, two, three or four days.

The vaginal pH of the women was recorded daily. Additionally, the women kept diaries recording the moisturizing effect of the composition, any discomforts experienced, and any leaking experienced. Leakage experienced was minimal within the first forty-eight hours of treatment demonstrating the bioadhesive capacity of a composition of the present invention.

Figure 6:
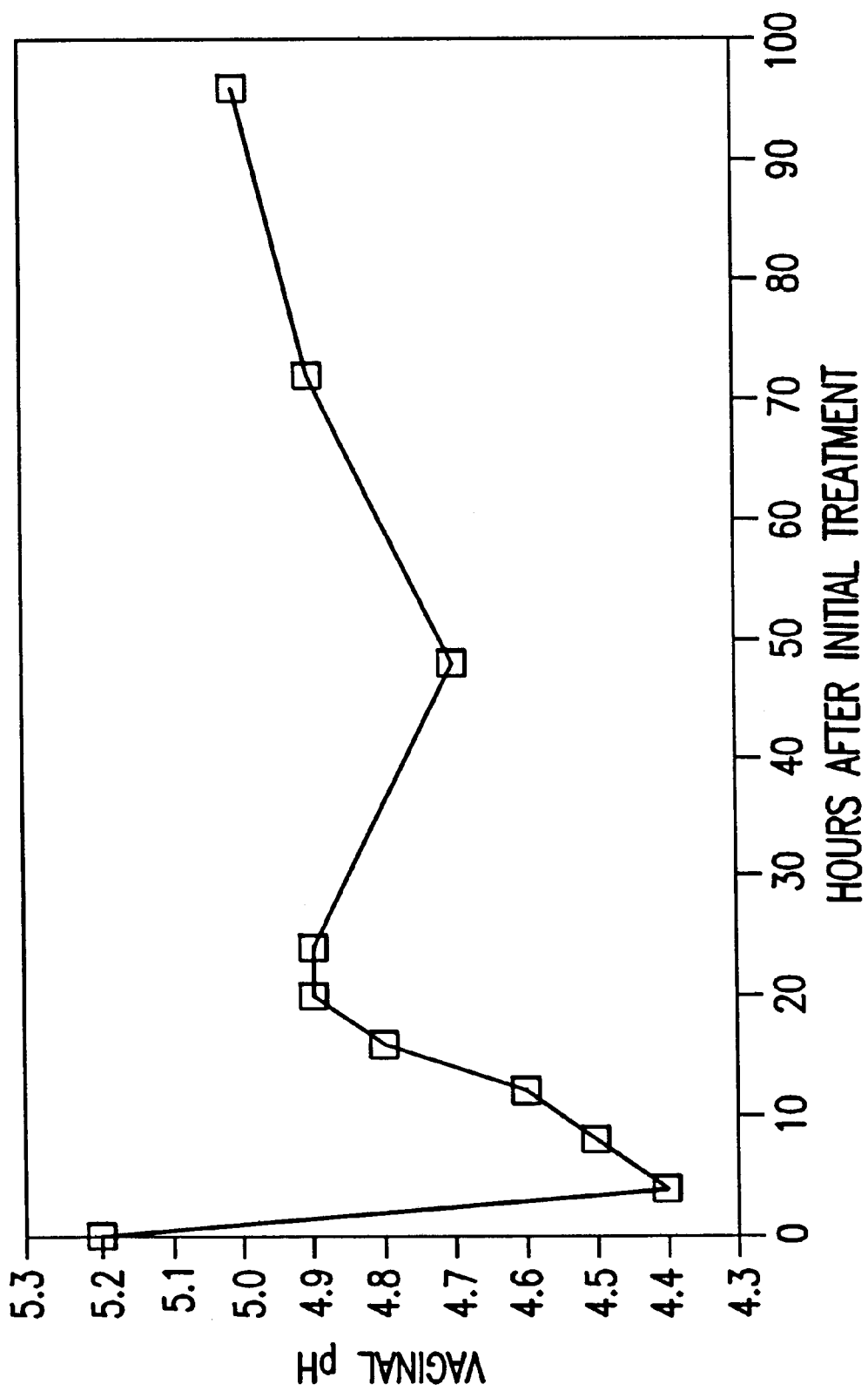
FIG. 6 is a graph illustrating the reduction of vaginal pH in women after one application of a composition of the present invention on day one.
Figure 7:
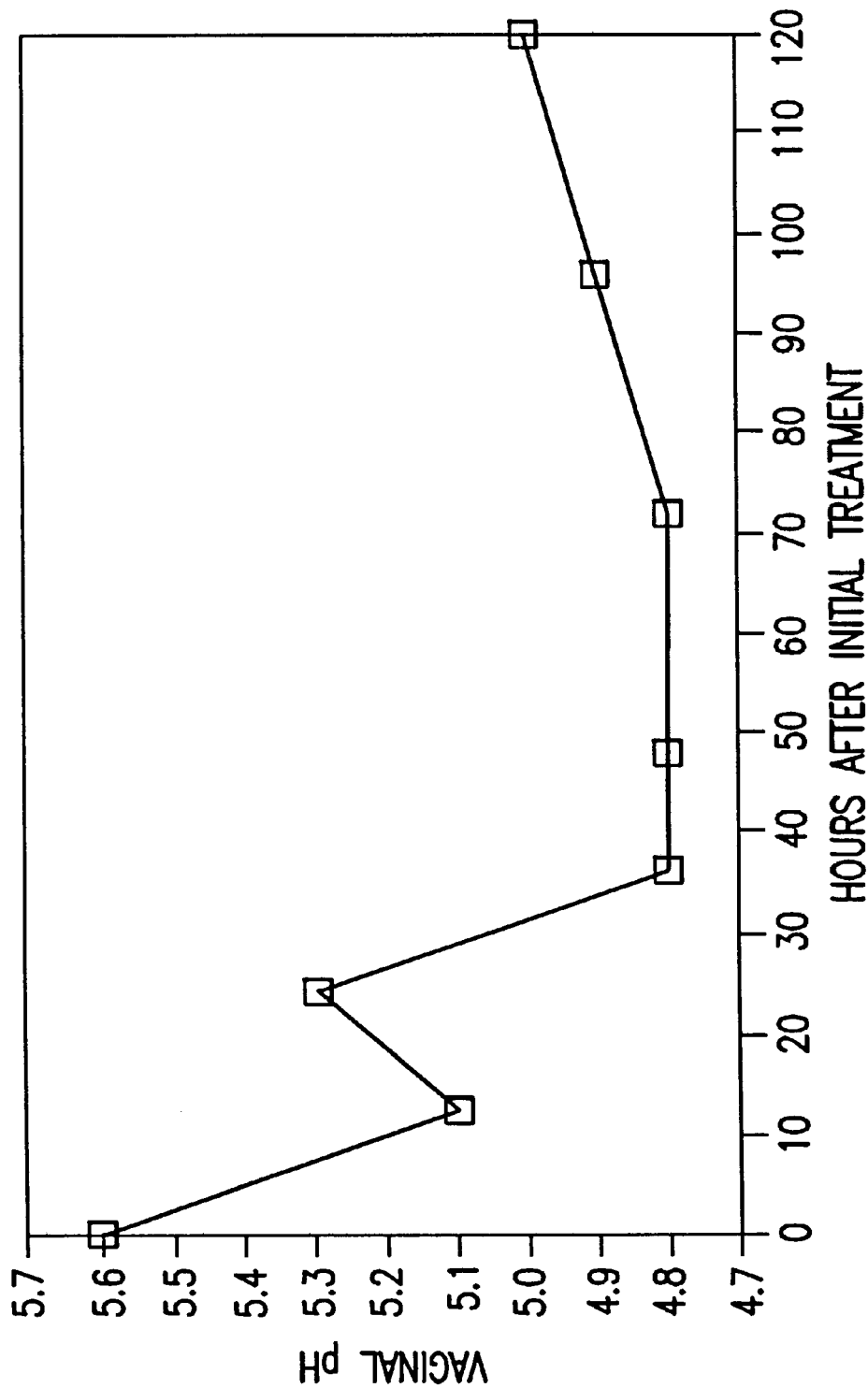
FIG. 7 is a graph illustrating the reduction of vaginal pH in women after one application of a composition of the present invention on each of the first two days.
Figure 8:
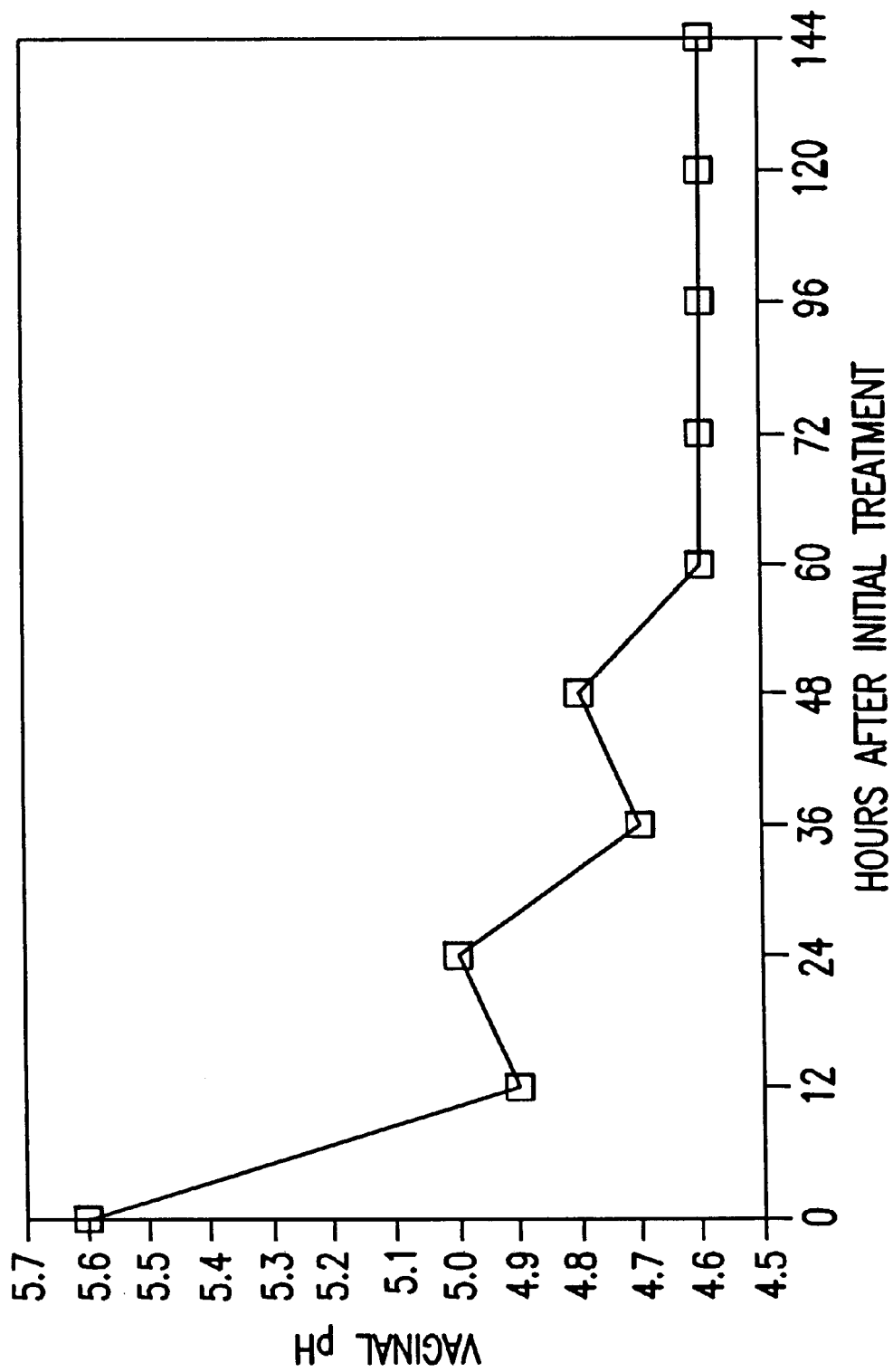
FIG. 8 is a graph illustrating the reduction of vaginal pH in women after one application of a composition of the present invention on each of the first three days.
Figure 9:
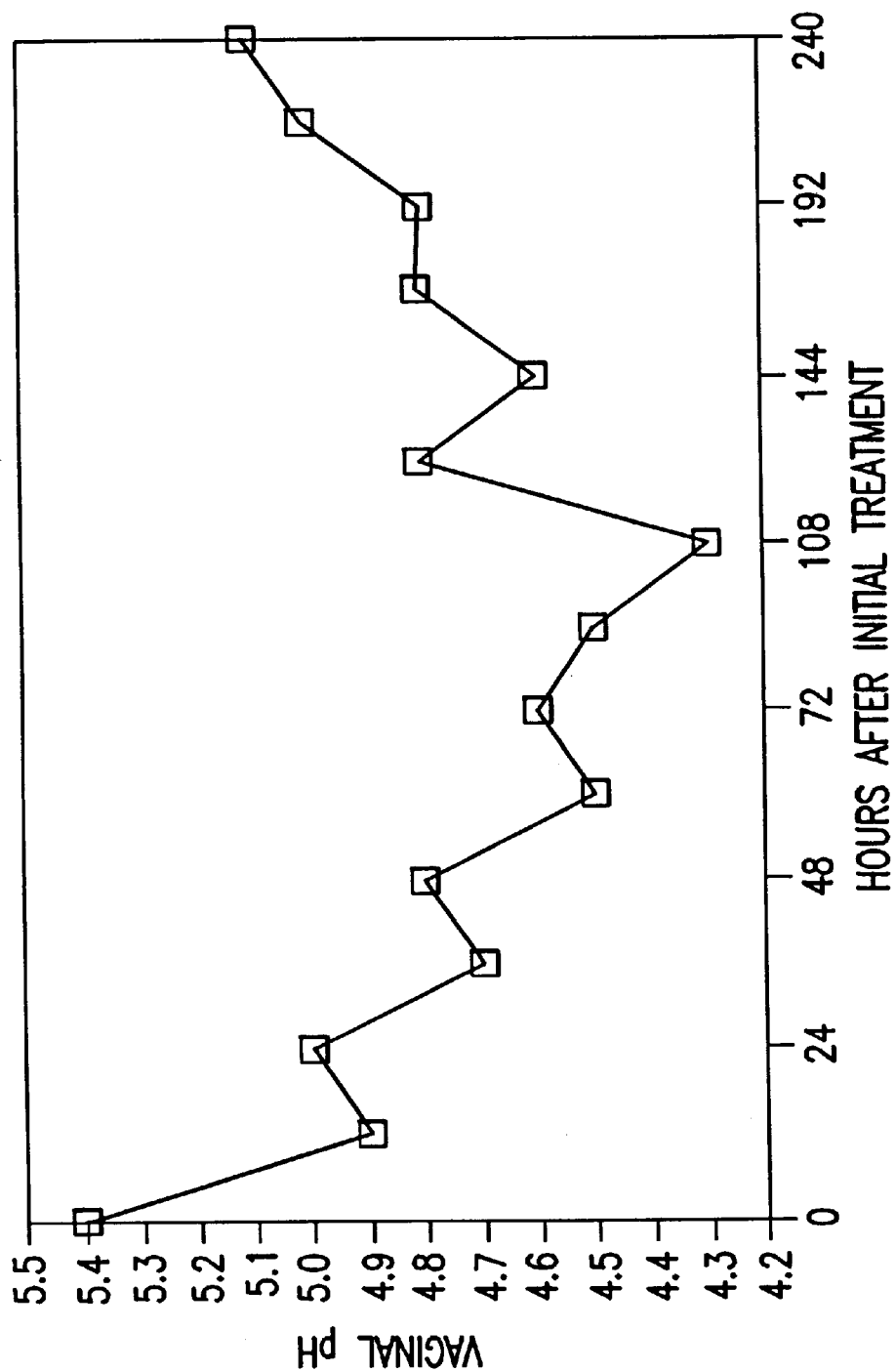
FIG. 9 is a graph illustrating the reduction of vaginal pH in women after one application of a composition of the present invention on each of the first five days.

The mean vaginal pH decreased relatively quickly, i.e., within the first four hours after application of the composition. See FIG. 6. Additionally, this low pH was maintained by consistent applications of the composition. See FIGS. 7–9 illustrating the results of the application of the composition over periods of two, three and five days, respectively.

We claim:

1. A method of treating bacterial vaginosis comprising (a) topically contacting the luininal surface of vaginal epithclial cells with an effective pH buffering amount of an aqueous compositions comprising water and an effective amout of a water-swellable, but water-insoluble, cross-linked pH buffering bioadhesive polymer wherein at least 80% of the monomers comprising said polymer contain at least one carboxyl group; and (b) maintaining said contact for a time period sufficient to lower the pH of the vagina to an acidic pH, said composition being free of treating agent.

2. The method according to claim 1 wherein at least 90% of the nmonomers comprising the polymer contain at least one carboxyl group.

3. The method according to claim 1 wherein the aqueous composition further comprises a consistency-ending agent.

4. The method according to claim 1 wherein the polymer comprises monomers at last 90% of which are acrylic acid.

5. The method according to claim 1 wherein the aqueous composition further comprises an adjuvant selected from the group consisting of preservatives, lubricating oils, emulsifying agents, coloring agents, odor-providing agents, and humectants.

6. The method according to claim 1 wherein the polymer is cross-linked with a cross-linking agent added to the polymer at about 0.01 to about 6 weight percent of the polymer.

7. The method according to claim 1 wherein said polymer is polycarbophil.

8. A method of buffering a mammalian vagina to a pH less than about 6.0 comprising (a) contacting the surface of vaginal epithelial cells with an effective pH buffering amount of an aqueous composition comprising water and an effective amounts of a water-swellable, but water-insoluble, pH-buffering bioadhesive cross-linked polymer wherein at least 80% of the monomers comprising said polymer contain at least one carboxyl group; and (b) maintaining said contact for a time period sufficient to lower the pH of the vagina to an acidic pH, said composition being free of treating agent.

9. The method according to claim 8 wherein said polymer is polycarbophil.

10. The method according to claim 8 wherein the polymer comprises monomers, at least 90% of which are acrylic acid.

11. The method according to claim 8 wherein the aqueous composition further comprises an adjuvant selected from the group consisting of preservatives, lubricating oils, emulsifying agents, coloring agents, odor-providing agents, and humectants.

12. The method according to claim 8 wherein the polymer is cross-linked with a cross-linking agent added to the polymer at about 0.01 to about 6 weight percent of the polymer.

13. The method according to claim 8 wherein the aqueous composition further comprises a consistency-enhancing agent.

* * * * *

UNITED STATES PATENT AND TRADEMARK OFFICE
CERTIFICATE OF CORRECTION

PATENT NO    :  6,017,521
DATED        :  Jan. 25, 2000
INVENTOR(S)  :  ROBINSON, et al

It is certified that errors appear in the above-identified patent and that said Letters Patent are hereby corrected as shown below:

In Column 18, line 7, "consistency-ending" should read --consistency-enhancing--

In Column 18, line 25, "amounts" should read --amount--

Signed and Sealed this

Tenth Day of April, 2001

*Attest:*

NICHOLAS P. GODICI

*Attesting Officer*    *Acting Director of the United States Patent and Trademark Office*

UNITED STATES PATENT AND TRADEMARK OFFICE
CERTIFICATE OF CORRECTION

PATENT NO.   : 6,017,521
DATED        : January 25, 2000
INVENTOR(S)  : Joseph R. Robinson William J. Bologna It is certified that error appears in the above-identified patent and that said Letters Patent is hereby corrected as shown below:

Column 17, claim 1,
Line 42, change "luininal" to -- luminal -- and change "epithclial" to -- epithelial --.
Line 44, change "compositions" to -- composition -- and change "amout" to -- amount --.

Signed and Sealed this

Eighteenth Day of September, 2001

*Attest:*

*Attesting Officer*

NICHOLAS P. GODICI
*Acting Director of the United States Patent and Trademark Office*